United States Patent [19]

Beaudoin et al.

[11] 4,312,216
[45] Jan. 26, 1982

[54] DEVICE FOR VIBRATING THE PIN OF A VISCOMETER

[75] Inventors: Paul Beaudoin, Vimory; Patrick Gilbert, Montargis; Jacques Petres, Grenoble, all of France

[73] Assignee: Commissariat a l'Energie Atomique, Paris, France

[21] Appl. No.: 161,737

[22] Filed: Jun. 23, 1980

[30] Foreign Application Priority Data

Jul. 24, 1979 [FR] France .............................. 79 19051

[51] Int. Cl.³ ............................................ G01N 11/16
[52] U.S. Cl. ....................................................... 73/54
[58] Field of Search ............................ 73/54, 59, 32 A

[56] References Cited

U.S. PATENT DOCUMENTS

| | | | |
|---|---|---|---|
| 2,340,507 | 2/1944 | Bjork | 73/59 |
| 2,973,639 | 3/1961 | Banks | 73/54 |
| 3,014,363 | 12/1961 | Labout | 73/59 |

*Primary Examiner*—James J. Gill
*Attorney, Agent, or Firm*—Pearne, Gordon, Sessions, McCoy & Granger

[57] ABSTRACT

The present invention relates to a device for vibrating the pin of a viscometer, wherein the emitter arm of the pin is fixed to the end of a spring leaf pivoted about a fixed point, said leaf abutting on a ball bearing whose inner race is moved in rotation by a drive shaft eccentric with respect to the axis of the bearing and whose outer race is locked in rotation. The invention is more particularly applied to vibrating viscometers of the type comprising a pin.

1 Claim, 2 Drawing Figures

DEVICE FOR VIBRATING THE PIN OF A VISCOMETER

The present invention relates to viscometers of the type comprising a pin and employing vibrations.

A vibrating viscometer is known to be an apparatus which comprises a pin immersed in the fluid to be studied, means for applying to the end of one of the arms of the pin a reciprocating vibration, means for measuring the vibration transmitted to the end of the other arm of the pin, and means for comparing the vibration applied and the vibration transmitted and particularly for measuring the phase shift between these two vibrations, which is a function of the viscosity of the liquid in which the pin is immersed.

More precisely, a vibrating viscometer is composed of a vibrating system constituted by a U-shaped pin of variable dimensions, on the arms of which the supple tubes which support it are generally welded. These tubes are themselves welded on a base. A motor is fixed on this base which, via a mechanical system, gives one of the arms of the pin (emitter arm), a sinusoidal reciprocating movement of determined frequency.

This movement is transmitted along the pin and up to the other arm (receiver arm) which therefore vibrates at the same frequency. If the system is not damped, the movement of this arm has the same phase and same amplitude as the energized arm; if the system is damped because it is immersed in a liquid, the movement of this receiver arm has a phase and an amplitude different from those of the energized emitter arm. It is the phase-shift existing between the two arms which is most often measured to ascertain the damping caused by the viscosity of the liquid in which the pin is immersed.

To detect the movement of the two arms of the pin, a magnet is generally fixed on each of them, which induces a voltage in a coil placed therebefore. With the aid of a phase meter, the phase difference existing between each of the arms of the pin is measured and the viscosity of the liquid in which the pin is immersed is deduced therefrom by calibration.

Such a vibrating viscometer may exist in different forms: however, reference may advantageously be made to Applicants' French Patent No. 76 16396 of May 31, 1976 to learn in greater detail the general design of such an apparatus to which the present invention is applied, it being understood that the field of application of the invention extends to all types of vibrating viscometers of the type comprising a pin.

In the apparatus of the type comprising a pin, which have just been described, the reciprocating movement necessary for energizing the emitter arm of the pin is generally obtained from a certain number of mechanical systems known for their capacity to convert a movement of rotation into a movement of translation.

The following mechanical systems may, for example, be mentioned: systems employing a cam, rod and spring, systems employing a rod, crank and crosshead as in steam engines or certain systems comprising a cam drum associated with a finger on which is fixed the end of the pin which is to be vibrated.

In other cases, the reciprocating movement of the emitter arm is effected by directly using the action of a magnetic field created in a coil by an A.C. or D.C. current, a core of soft iron or a magnet moving in the axis of said coil.

However, the two types of systems heretofore envisaged have certain drawbacks.

In the purely mechanical systems, frictions reduce the overall yield. When pivots exist, they are difficult to lubricate due to the extreme smallness of the amplitude of the necessary movement and they wear out rapidly, this reducing the life of the apparatus. Furthermore, in any mechanical system, the inevitable operational clearances add up for the different components of the whole and end up by creating a considerable lack of precision in the final result obtained. Now, it is extremely important in apparatus of this type that the amplitude of the movement as well as its frequency be constant with a high degree of precision.

The electromagnetic devices heretofore described obviously eliminate the problems of friction, and this may appear to be an advantage. Unfortunately, the amplitude of the reciprocating vibration obtained by such systems is directly a function of the mechanical load applied on the pin and therefore of the total inertia of the whole of the pin immersed in the liquid. As it has been seen that the measuring process necessitated a perfectly constant amplitude of the vibration whatever the load applied to the pin, this results in such systems also presenting appreciable specific drawbacks.

It is an object of the present invention to provide a device for vibrating the pin of a vibrating viscometer which overcomes the above-mentioned drawbacks of the systems of the prior art, whilst being completely reliable and particularly simple to use.

This device is essentially characterised in that the emitter arm of the pin is fixed to the end of a spring leaf pivoted about a fixed point, said leaf abutting on a ball bearing whose inner race is moved in rotation by a drive shaft eccentric with respect to the axis of the bearing and whose outer race is locked in rotation under the effect of a powerful magnet fixed on said spring leaf and maintaining said latter in permanent contact with said outer race, at a fixed point thereof.

The device forming the subject matter of the invention is derived from the mechanisms of the cam, rod, spring family, but the essential feature consists in using as eccentric cam a ball bearing of which only the inner race is mobile about a drive shaft eccentric with respect to the axis of the ball bearing itself. The outer race, in direct contact with the spring leaf bearing the emitter arm of the pin, is maintained locked in rotation with respect to its axis and fixed with respect to the spring leaf due to the presence thereon of a very powerful permanent magnet which holds it in place along the spring leaf. The ball bearing thus describes, with respect to the surrounding space, a movement of rotation-translation about the eccentric drive shaft which moves the pin of the viscometer in reciprocating motion. For small amplitudes, this reciprocating movement, which in fact is made over an arc of circumference, is assimilable to a rectilinear movement.

As in the prior devices, the rod is pivoted via a spring leaf about a fixed point, this eliminating the problems of lubrication and wear and tear encountered with conventional pivots.

In the device according to the invention, the only friction which occurs is that of the ball bearing and it is consequently reduced to the strict minimum necessary, as only the inner race of the bearing is animated by a rotating movement. The outer race of the same bearing rolls slightly without sliding on either side of its point of contact with the spring leaf, on two plates of tempered metal in which the permanent magnet is mounted.

Wear and tear and clearances are also reduced to a minimum since the only residual clearance is that of the eccentric bearing.

In accordance with the invention, the rotary motor may be of any known type, synchronous or asynchronous, but if it is asynchronous, it should be chosen to be overpowerful so that its slide is substantially constant. A step by step electric motor may also be used in continuous rotation, this allowing a variable speed, therefore a variable vibration frequency and a more extensive range of measurement.

It should further be noted that the vibrating device according to the invention necessitates, like the comparable devices of the prior art, that the ratio of the length of the rod with respect to the necessary amplitude be as large as possible, in order that the displacement of the emitter arm of the pin may be assimilated to a segment of a straight line.

Finally, among the advantages of the device, it may be used at temperatures very different from one another, without substantially changing its modus operandi, as expansions are freely allowed and cannot cause any undesirable parasitic stress to appear.

The invention will be more readily understood on reading the following description with reference to the accompanying drawings, in which.

Figure 1:
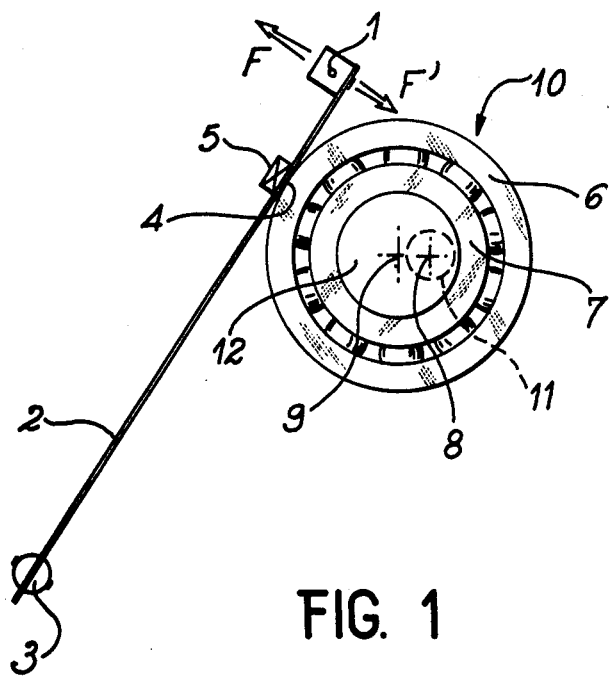
FIG. 1 is a plan view of the device according to the invention.
Figure 2:
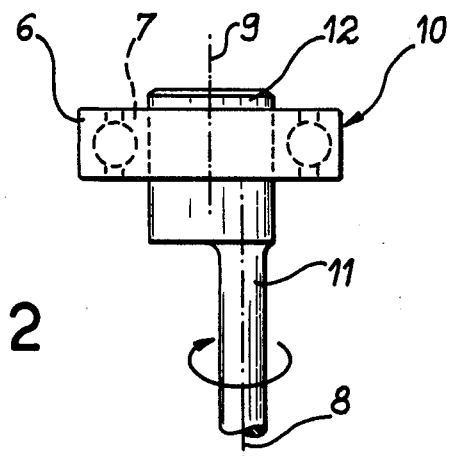
FIG. 2 shows a view in elevation of the device of FIG. 1.

Referring now to the drawings, FIG. 1 shows the pin 1 fixed to the end of a spring leaf 2 movable about a point of fixation 3. The spring leaf 2 abuts on a fixed point 4 via the magnet 5 on the outer race 6 of a ball bearing whose inner race 7 is rotatable about the axis 8 of the ball bearing 10, eccentric with respect to axis 9. To this end, a drive shaft 11 drives an eccentric cam 12 on which is fixed the inner race 7 of the bearing 10.

In accordance with the invention, the magnet 5 is chosen to be sufficiently powerful to fix the outer race 6 of the ball bearing 10 at point 4 and to lock it in rotation about the axis 9 in contact with the spring leaf 2. To this end, in a preferred embodiment of the invention, the permanent magnet 5 is mounted between two plates of tempered metal which are made fast with the spring leaf 2. The functioning of the device is then particularly simple: when the drive shaft 11 rotates at determined constant speed, the inner race 7 of the bearing 10 then rotates about the eccentric axis 8, this driving the fixed outer race 6 in a reciprocating movement of translation-rotation, which in turn reverberates in the directions of arrows FF' on the emitter arm of the pin 1 which then vibrates by a reciprocating movement at the same frequency.

The choice of the motor for moving the shaft 11 may be made as a function of the following criteria:

If the motor is asynchronous, it must be over-dimensioned so that the slide remains the same at each instant, even if the load imposed on the pin varies. If the frequency of the mains does not vary, the speed of rotation is then constant, as well as the energization frequency of the pin 1.

If the motor is synchronous, with hysteresis, or if it is synchronous, oriented, with permanent magnet, the speed obtained is then in strict synchronism with the supply frequency of the A.C. electric network mains and the desired precision is obtained without difficulty.

If the motor is of the step by step type, the speed of rotation is then determined by the electronic means for controlling the motor, this generally enabling a strictly constant speed to be obtained without difficulty. Moreover, by acting precisely on these electronic control means, an adjustable frequency in a more extensive range may then be easily obtained.

What is claimed is:

1. In a vibrating viscometer of the type comprising a U-shaped pin composed of two arms, namely an emitter arm and a receiver arm, a device for vibrating the pin, wherein the emitter arm thereof is fixed to the end of a spring leaf pivoted about a fixed point, said leaf abutting on a ball bearing whose inner race is moved in rotation by a drive shaft eccentric with respect to the axis of the bearing and whose outer race is locked in rotation under the effect of a powerful magnet fixed on said leaf and maintaining the latter in permanent contact with said outer race, at a fixed point thereof.

* * * * *